(12) United States Patent
Nenov

(10) Patent No.: US 6,416,480 B1
(45) Date of Patent: Jul. 9, 2002

(54) METHOD AND APPARATUS FOR AUTOMATED ACQUISITION OF THE GLASGOW COMA SCORE (AGCS)

(76) Inventor: Valeriy Nenov, 6597 Kentwood Bluffs Dr., Los Angeles, CA (US) 90045

( * ) Notice: Subject to any disclaimer, the term of this patent is extended or adjusted under 35 U.S.C. 154(b) by 0 days.

(21) Appl. No.: 09/535,264

(22) Filed: Mar. 23, 2000

Related U.S. Application Data
(60) Provisional application No. 60/126,945, filed on Mar. 29, 1999.

(51) Int. Cl.$^7$ .................................................. A61B 5/00
(52) U.S. Cl. ...................................... 600/557; 600/300
(58) Field of Search .............................. 600/300, 557, 600/483, 376, 544, 383, 546; 607/5, 72; 704/255

(56) References Cited
U.S. PATENT DOCUMENTS

| | | | |
|---|---|---|---|
| 3,706,308 A | * 12/1972 | John et al. | 600/483 |
| 4,713,777 A | * 12/1987 | Klovstad et al. | 704/255 |
| 5,381,805 A | * 1/1995 | Tuckett et al. | 600/557 |
| 5,447,166 A | * 9/1995 | Gevins | 600/544 |
| 5,571,150 A | * 11/1996 | Wernicke et al. | 607/72 |
| 5,724,968 A | * 3/1998 | Iliff | 600/300 |
| 5,755,230 A | * 5/1998 | Schmidt et al. | 600/376 |
| 6,032,065 A | * 2/2000 | Brown | 600/383 |
| 6,148,233 A | * 11/2000 | Owen et al. | 607/5 |

FOREIGN PATENT DOCUMENTS
EP 013183 A1 * 12/1979

* cited by examiner

Primary Examiner—Eric F. Winakur
Assistant Examiner—David McCrosky
(74) Attorney, Agent, or Firm—Daniel L. Dawes; Myers, Dawes & Andras LLP

(57) ABSTRACT

A system and a method for computerized automated acquisition of the Glasgow Coma Score (GCS) for quantifying level of consciousness following traumatic brain injury performs the assessment of the GCS of critically ill patients on a periodic basis. Based on measurement of stimulus-induced standard physiological and verbal responses of the patient such as EMG, EOG and simple utterances, the system produces a coma score, which corresponds one-to-one with the score obtained by human assessors. The apparatus used for automated assessment of a degree of consciousness in a patient comprises a computer having a program stored therein to assess consciousness of the patient, at least one electrode coupled to the computer for sensing a physical response, a speaker coupled to the computer for producing an audio signal, a microphone coupled to the computer configured to sense an audio response from the patient, and a pain stimulator coupled to the computer to generate a pain stimulus in the patient. The method used for automated assessment of a degree of consciousness in a patient using a computer comprises the steps of sensing a response from the patient, recording the response in the computer, the response being characterizable in nature, analyzing the characterizable nature of the response to determine the nature in the computer, categorizing the nature of the response in the computer, and producing by the computer a stimulus dependent on the categorization of the response.

32 Claims, 6 Drawing Sheets

Eye Opening (E)

Spontaneous = 4  Responds to speech = 3  Responds to pain = 2  No response = 1

Motor Response (M)

Obeys commands = 6  Abnormal Flexor Response = 3  Withdraws = 4  Abnormal Extensor Response = 2  No response = 1

Verbal Response (V)

Oriented = 5

Confused "1968" = 4
Inappropiate words "my dog" = 3
Incomprehensible sounds = 2
No response = 1

AGCS Time Line

FIG. 5A — Normal

| | 1 | | | | 2 | | | | 3 | | | | 4 | | | | 5 | | | |
|---|---|---|---|---|---|---|---|---|---|---|---|---|---|---|---|---|---|---|---|---|
| | S | R | A | C | S | R | A | C | S | R | A | C | S | R | A | C | S | R | A | C |
| Pain Stim | | | | | | | | | | | | | | | | | | | | |
| Verbal Stim | | | | | (4) | | | | (6) | | | | | | | | | | | |
| 4 E EOG Rec | | | | E4 | | | | | | | | | | | | | | | | |
| 5 V Verb Rec Label | | | | | | | | V5 | | | | | | | | | | | | |
| 6 M EMG Rec | | | | | | | | | | | | M6 | | | | | | | | |

15

FIG. 5B — Mild HT

| | 1 | | | | 2 | | | | 3 | | | | 4 | | | | 5 | | | |
|---|---|---|---|---|---|---|---|---|---|---|---|---|---|---|---|---|---|---|---|---|
| | S | R | A | C | S | R | A | C | S | R | A | C | S | R | A | C | S | R | A | C |
| Pain Stim | | | | | | | | | | | | | | | | | | | | |
| Verbal Stim | | | | | (2) | | | | (4) | | | | (6) | | | | | | | |
| 3 E EOG Rec | | | | NO | | | | E3 | | | | | | | | | | | | |
| 4 V Verb Rec | | | | | | | | | | | | V4 | | | | | | | | |
| 6 M EMG Rec | | | | | | | | | | | | | | | | M6 | | | | |

>8

FIG. 5C — Severe HT

| | 1 | | | | 2 | | | | 3 | | | | 4 | | | | 5 | | | |
|---|---|---|---|---|---|---|---|---|---|---|---|---|---|---|---|---|---|---|---|---|
| | S | R | A | C | S | R | A | C | S | R | A | C | S | R | A | C | S | R | A | C |
| Pain Stim | | | | | | | | | (3) | | | | | | | | | | | |
| Verbal Stim | | | | | (2) | | | | | | | | | | | | | | | |
| 2 E EOG Rec | | | | NO | | | | NO | | | | E2 | | | | | | | | |
| 2 V Verb Rec | | | | | | | | | | | | V2 | | | | | | | | |
| 3 M EMG Rec | | | | | | | | | | | | M3 | | | | | | | | |

<8

FIG. 5D — Brain Death

| | 1 | | | | 2 | | | | 3 | | | | 4 | | | | 5 | | | |
|---|---|---|---|---|---|---|---|---|---|---|---|---|---|---|---|---|---|---|---|---|
| | S | R | A | C | S | R | A | C | S | R | A | C | S | R | A | C | S | R | A | C |
| Pain Stim | | | | | | | | | (3) | | | | | | | | | | | |
| Verbal Stim | | | | | (2) | | | | | | | | | | | | | | | |
| 1 E EOG Rec | | | | NO | | | | NO | | | | E1 | | | | | | | | |
| 1 V Verb Rec | | | | | | | | | | | | V1 | | | | | | | | |
| 1 M EMG Rec | | | | | | | | | | | | M1 | | | | | | | | |

3

---

S Stimulate    Pain stimulation is needed IF (E le 2) or (V le 2) or (M le 5)
R Record
A Analyse    The numbers (2), (3), (4), (6) and (7) represent different
C Categorize    types of stimulation as shown on the AGCS Flowchart

METHOD AND APPARATUS FOR AUTOMATED ACQUISITION OF THE GLASGOW COMA SCORE (AGCS)

Related Applications

The present application is related to U.S. Provisional Patent Application Ser. No. 60/126,945, filed on Mar. 29, 1999, which is incorporated herein by reference.

BACKGROUND OF THE INVENTION

1. Field of the Invention

The present invention relates to systems and methods for computerized monitoring the levels of consciousness of patients admitted to medical units such as intensive care units, emergency rooms, operating rooms, etc. Specifically it automates and ultimately completely eliminates the need for human assessment of the most commonly used coma score—the Glasgow Coma Score (GCS), while still using the same scale.

2. Description of the Prior Art

The Glasgow Coma Scale (GCS) was proposed by Teasdale and Jennett (Teasdale and Jennett 1974) and further elaborated Avezaat et. al., "A Scoring Device For The Level Of Consciousness: The Glasgow "Coma" Scale" *Ned Tijdschr Geneeskd* 121 2117–21 (1977). GCS is the most widely used scoring system in quantifying level of consciousness following traumatic brain injury. It is used primarily because it is simple, has a relatively high degree of inter-observer reliability, and because it correlates well with outcome following severe brain injury.

GCS is comprised of three components: eye opening—E; motor response—M; and verbal response—V. (1) The eye opening is scored on a scale from 1 to 4. A score of 1 is assigned to a patient who is incapable of opening his or her eyes. In contrast, a 4 is assigned if the patient opens his or her eyes spontaneously. If a patient is unable to open his/her eyes spontaneously, but is capable of responding to verbal commands, such as "open your eyes", a score of 3 is assigned. If eye opening cannot be elicited by a verbal command, but can be caused by applying a painful stimulus, the response is scored as 2.

(2) The motor response is scored on a scale from 1 to 6. A maximum score of 6 is assigned to a patient capable of obeying verbal commands such as "Show me two fingers". If the patient does not react to verbal commands, but can localize painful stimuli by moving his or her arm toward the pain source in an attempt to remove the irritant, he or she will receive a score of 5. A patient only capable of a withdrawal response (a reflexive non-localizing movement) is assigned a score of 4. A score of 3 is given to an abnormal flexion response in which the arms are flexed at the elbows. If the motor response is an abnormal rigid extension ("brain stem level") the score is 2. A minimum score of 1 is assigned to a patient who produces no motor response to verbal or pain stimulus.

(3) The verbal response is scored on a scale from 1 to 5. A maximal verbal score of 5 is given to a patient who is oriented and converses cohesively. A patient who can speak intelligibly, but is disoriented (i.e., unable to answer questions such as "Who are you?" or "Where are you?") is assigned a verbal score of 4. A score of 3 is given to a patient who utters inappropriate words in response to verbal questions. If the patient produces only incomprehensible sounds he or she will receive a score of 2. The absence of a verbal response is designated as 1 on the verbal scale. Often patients in the ICU are intubated; resulting in a mechanical obstruction of their airways which prevents them from speaking. In such cases a verbal score of 1 v is logged. The total maximal Glasgow Coma Score is 15 while the minimal score is 3. Table 1 is a summary of the Glasgow Coma Scale.

TABLE 1

Summary of the Glasgow Coma Scale

| Eye Opening (E) | Best Verbal Response (V) | Best Motor Response (M) upper limbs |
|---|---|---|
| 4 = Spontaneous | 5 = Normal conversation (oriented) | 6 = Normal (obeys commands) |
| 3 = To voice | 4 = Disoriented incoherent conversation | 5 = Localizes to pain |
| 2 = To pain | 3 = Words, but not coherent | 4 = Withdraws to pain (normal flexion) |
| 1 = None | 2 = No words, incomprehensive only sounds | 3 = Decorticate posture (abnormal flexion) |
|  | 1 = None | 2 = Decerebrate (extension) |
|  |  | 1 = None |
|  |  | Total GCS = E + V + M |

The following example demonstrates a GCS assessment performed on a comatose patient. Prior to the GCS assessment the patient is situated in a standard position (hands on either side of the chest). The nurse is unable to observe spontaneous eye movements and subsequently determines that the patient is unconscious. In an attempt to elicit a response the nurse gives verbal commands such as "Jack open your eyes". This is repeated few times, each time successively louder. The patient's eyes remain closed, however, so she proceeds to forcefully pinch (i.e., painfully) the skin on his shoulders (above the deltoid muscle). The patient does not localize the pain (does not move hand toward the pain source), so the nurse pinches skin on the inner side of his biceps, which the patient localizes, or tickles the patient's nose with a Q-tip—an irritant which is localized as well. This is the end of the GCS exam. The patient was scored as GCS 7-8v (E2; M4-5; V1v).

FIG. 1 shows a cartoon view of the standard GCS assessment procedure as performed by nurses in hospitals around the world. It shows the various eyes, motor, and verbal responses as observed during GCS assessment.

The GCS assessment is part of standard patient care and is commonly incorporated in most hospitals' written Policies and Practices manual. Specifically, in a neurosurgery ICU the GCS of every patient is assessed and manually recorded in the patient's chart every hour or entered in a computer. Routinely, an attending nurse performs the procedure; however, the attending physician can also assess the GCS during his or her rounds. Normally it takes about two to five minutes to get the GCS depending on the patient's state of consciousness. Besides neurosurgery ICUs, where the patients are usually in a somewhat impaired state of consciousness or comatose, the assessment of GCS is recommended every 4 hours in all non-neurological ICUs and a minimum of once a shift for patients on the hospital floor. GCS is also commonly used in the emergency room.

There are several reasons why it is desirable to have an automated method for measuring the GCS:

1) Availability of qualified human assessors: Unpredictable changes of the patient's level of consciousness can occur any time, day and night, and critical care personnel might not always be at hand to capture such changes. An AGCS system can be programmed to assess the GCS automatically and repetitively as frequently as necessary.

2) Subjectivity and frequency of assessment: Since the assessment of GCS requires human intervention (clinical procedure by nurses or doctors), it is often subjective, and can not be always performed on a regular basis.

3) Variability and accuracy: The accuracy of the Glasgow Coma Score is critical. Despite its demonstrated reproducibility in published works, in actual practice there is substantial variability in performing, scoring and recording the GCS by bedside nurses (these are the health care workers who most frequently perform this test as a routine evaluation). It is not at all uncommon to see an abrupt change in the recorded GCS when there is "change of shift", when a new nurse comes on duty: "Scoring is often performed incorrectly (e.g. nurses commonly and inappropriately score patients according to worst response" and therefore it is often inaccurate.

4) Reliability and reproducibility of the GCS in actual practice is important for physician monitoring of patient status. Decisions regarding non-invasive or invasive diagnostic testing or therapeutic management are often made based on changes in GCS. For instance, a significant (e.g., 2 point) decrease in GCS often will lead to the performance of a cranial CT scan, or an invasive cerebral angiogram, which may further result in a change in the patient's treatment. If the GCS has been scored inaccurately, the patient will have been exposed to a potentially risky and unnecessarily costly procedure, or conversely, a change in mental state with implications for early intervention may be missed. The AGCS system will reliably and reproducibly provide the Glasgow coma score.

5) Inadequate personnel training for GCS assessment: Many patients with neurological problems, such as, stroke following coronary artery bypass surgery are managed in non-neurological/neurosurgical intensive care units. The nurses in these units do not have extensive training in neurological assessment and in the GCS. Neurological monitoring in such patients is therefore often sub-optimal and inaccurate. The GCS scoring is an important part of the initial assessment of patients sustaining acute brain injury from trauma. However, emergency department personnel often are not experienced at administering and scoring the GCS, and it often is recorded inaccurately. Furthermore, the multitude of activities which go on in the middle of an acute trauma resuscitation often make the performance, and particularly the repeated performance, of the GCS difficult.

Based on these reasons we believe that having an Automated Glasgow Coma scoring method and system available would be of great benefit in such situations. We further believe that such a system will be particularly attractive to the critical care community because the GCS is the most commonly and widely used scoring system today for quantifying the level of consciousness following traumatic brain injury (TBI).

Different coma scales have been proposed and used in a number of countries around the world. Some of the more notable are the Swedish Reaction Level Scale (RLS 85) Starmark et.al., "The Reaction Level Scale (Rls 85) Manual And Guidelines" *Acta Neurochir* 91 12–20 (1988), the Innsbruk Coma Scale (ICS) Benzer et.al., *"Prediction Of Non-Survival After Trauma: Innsbruck Coma Scale" Lancet* 338 977–8 (1991), the Munich Coma Scale (MCS) (Brinkmann et al 1976), the Canadian Neurological Scale Cote et.al. "The Canadian Neurological Scale: Validation And Reliability Assessment" *Neurology* 39 638–643 (1989), the Glasgow-Liege Scale (GLS), which is an attempt to improve upon the GCS, Born "The Glasgow-Liege Scale: Prognostic Value And Evolution Of Motor Response And Brain Stem Reflexes After Severe Head Injury" *Acta Neurochirurgica* 91 1–11 (1988), the Edinburg-2 coma scale Sugiura et.al., "The Edinburgh-2 Coma Scale: A New Scale For Assessing Impaired Consciousness" *Neurosurgery* 12 411–5 (1983), and others. The effectiveness of the Glasgow Coma Scale has been compared to several of these scales (e.g., Johnstone et.al. "A Comparison Of The Glasgow Coma Scale And The Swedish Reaction Level Scale" *Brain Injury* 7 501–506 (1993); (Sugiura et al 1983), Hall et.al. "Characteristics And Comparisons Of Functional Assessment Indices: Disability Rating Scale, Functional Independence Measure, And Functional Assessment Measure" *Journal of Head Trauma Rehabilitation* 8 60–74 (1993). Alternatives to the GCS in the form of continuous performance tests have also been proposed, Wijdicks et.al., "Measurement Of Impaired Consciousness In The Neurological Intensive Care Unit: A New Test" *Journal of Neurology Neurosurgery and Psychiatry* 64 117–119 (1998).

It should be emphasized that GCS is not used to substitute for the comprehensive neurological exam, but rather to screen for the necessity of performing it Segatore et.al. "The Glasgow Coma Scale: Time For Change" *Heart Lung* 21 548–57 (1992) at pp. 556. Furthermore, there are several limitations of GCS, particularly in its middle range (Segatore and Way 1992). Unless it is administered by experienced professionals, it may lack reliability Morris, "Assessment And Communication Of Conscious Level: An Audit Of Neurosurgical Referrals" *Injury* 24 369–72 (1993), Rowley et.al. "Reliability And Accuracy Of The Glasgow Coma Scale With Experienced And Inexperienced Users" *Lancet* 337 535–8 (1991). It can be affected by a number of factors such as poisoning Chan et.al., "The Use Of Glasgow Coma Scale In Poisoning" *J Emerg Med* 11 579–82 (1993) or paresis Proehl "The Glasgow Coma Scale: Do It And Do It Right" *J Emerg Nurs* 18 421–3 (1992). Nonetheless, while clearly not perfect, the GCS is widely used and indeed is the current standard of care in ICUs. Thus, its automation as proposed in this invention provides a useful adjunct in monitoring the status of comatose patients.

There are a number of technical developments in the fields of physiological monitoring both EMG and EOG, speech recognition/generation as well as in patient pain stimulation/modulation/control. The electromyogram, (EMG), refers to voltage potentials recorded from muscle(s), and the electrooculogram, (EOG), refers to voltage potentials recorded during eye movements. Many of these developments are described in the literature, and patents cover some. However, to our knowledge, presently there is no publication or patent, which has put together relevant prior art is such a fashion as to realize the AGCS method and device as presented below. There are only a few patents in the US Patent Office database which contain the keywords "Glasgow" and "Coma". GCS is mentioned in these patents only as a clinically relevant parameter monitored in the ICU. None of these patents, however, addresses even remotely the invention disclosed below.

There are numerous patents in the fields of signal processing and pattern matching and more specifically patents that relate to EEG, EMG and EOG. For instance Pardey, reported in Pardey et.al. "Physiological Monitoring", in US Patent Office (USA: USA) (1999) describes a system for monitoring insomnia or vigilance which employs a neural network to analyze electrical signals recorded from the patient and assign sleep or wakefulness stages and generate a hypnogram.

A method and device for evaluating an EEG carried out in the context of anesthesia and the intensive care unit was described by Schultz as reported in Schultz et.al. "Method And Device For Evaluating An EEG Carried Out In The Context Of Anaesthesia Or Intensive Care", U.S. Pat. No. 6,011,990 (2000). In this system, multivariate statistical methods are used to classify EEG patterns into clinically relevant behavioral states (e.g., waking, subvigilance, sleepiness, sleep, anesthesia, coma, etc.) of anaesthetized or critically ill patients. The system, however, does not produce a coma score.

Publications and patents in the field of voice recognition, and speech generation are also ubiquitous. In fact, there are also commercially available devices capable of accomplishing the voice generation/recognition tasks as they relate to the AGCS system. For instance, the Dragon software, or the IBM voice recognition package can be used as the voice recognition component of AGCS. Such technology is hereby incorporated by reference as prior art and we do not have any claims on it.

There are numerous papers, Tsen et.al. "Transcutaneous Electrical Nerve Stimulation Does Not Augment Combined Spinal Epidural Labor Analgesia [In Process Citation]" *Can J Anaesth* 47 38–42 (2000); Coates, "Transcutaneous Electrical Nerve Stimulation: Tens—Practical Guidance On Application" *Pract Midwife* 1 12–4 (1998) and several devices on the market for pain stimulation, modulation and assessment of the patients' sensitivity to pain. Transcutaneous Electrical Nerve Stimulators (TENS) and variations thereof, are manufactured and sold by companies. Thermal pain stimulators are available from Medoc, Ltd. (http://medoc-web.com/pain.html) and have been described in the literature (Allen et.al. "Noxious Cutaneous Thermal Stimuli Induce A Graded Release Of Endogenous Substance P In The Spinal Cord: Imaging Peptide Action In Vivo" *J Neurosci* 17 5921–7 (1997); Willer et al "Encoding Of Nociceptive Thermal Stimuli By Diffuse Noxious Inhibitory Controls In Humans" *J Neurophysiol* 62 1028–38 (1989). Again, such devices are incorporated here by reference.

There is no similar method or device for assessment of the GCS on the market or in the literature at present. Furthermore, presently there is no system on the market, which combines behavioral and physiologic observations into a net assessment of the level of consciousness.

BRIEF SUMMARY OF THE INVENTION

The present invention comprises a method and a system which are provided for automated computerized assessment of the Glasgow Coma Score (GCS). What is disclosed is a method and a computerized system that automatically and reliably maps stimulus-induced physiologic measurements to the GCS. This system is no harder to use, nor more invasive, than current monitoring for vital signs in the ICU and therefore can be adopted in clinical practice. The AGCS method and system disclosed collects physiological data such as EMG and EOG as well as speech data, which are digitized and stored on-line.

There are three integrated functions that are performed by the AGCS system: (1) patient stimulation; (2) data acquisition; and (3) data analysis. Computer-controlled verbal or pain stimulators provide patient stimulation. The acquired data is continuously analyzed on-line. Physiological and speech data are automatically interpreted and mapped online to the Glasgow Coma Scale. An algorithm, which implements a decision tree is modeled after the decision process used achieves this by human assessors. The tree is traversed in real time during the process of the AGCS estimation. The term real-time describes a system 10 with negligible latency between input and output.

The nodes of this decision tree are stimulus/response pairs (tests) and its branches implement the logic of the standard Glasgow Coma assessment procedure. The end-leafs of the tree correspond to the possible GCS outcomes (4 in the Eye response, 5 in the Verbal, and 6 in the Motor). In addition, if the algorithm can not come to a definite classification of the patient's responses, it automatically requests an additional assessment or notifies the nurse.

More specifically the invention is an apparatus for automated assessment of a degree of conscious in a patient comprising a computer having a program stored therein to assess consciousness of the patient. At least one sensor is coupled to the computer for sensing a patient response. At least one stimulator is coupled to the computer to generate a stimulus applied to the patient.

The sensor comprises at least one electrode coupled to the computer for sensing a physical response or movement and/or a microphone coupled to the computer configured to sense an audio response from the patient. The stimulator comprises a speaker coupled to the computer for producing an audio signal and/or a pain stimulator coupled to the computer to generate a pain stimulus in the patient.

The electrode or electrode assembly comprises an EMG and/or EOG electrode and associated electronics such as an amplifier and an A-to-D converter. The program stored in the computer provides the computer with a capability to record movement of the patient as sensed by the at least one electrode in response to a verbal cue provided by the computer through the speaker.

The program stored in the computer provides the computer with speech recognition capability of the audio response from the patient from the microphone which has the capability to recognize normal conversation, coherent speech, and/or the capability to recognize words included in the audio response from the patient. The program stored in the computer provides the computer with a capability to record audio responses from the patient as sensed by the microphone in response to a verbal cue provided by the computer through the speaker.

The program stored in the computer provides the computer with a capability to record movement from the patient as sensed by the at least one electrode and to produce a verbal cue through the speaker in response to the recorded movement.

The program stored in the computer provides the computer with a capability to produce a verbal cue through the speaker to record movement or lack thereof from the patient as sensed by the at least one electrode, and in response to the recorded movement or lack thereof to generate the pain stimulus through the pain stimulator.

The computer performs cycles comprising stimulation of the patient, recordation of patient response, analysis of patient response and categorization of patient response in which the pain stimulator or speaker is selectively activated to provide a stimulus beginning in a subsequent cycle dependent on categorization of patient response in a prior cycle.

The invention is also defined as a method of automated assessment of a degree of consciousness in a patient using a computer comprising the steps of sensing a response from the patient. The response is recorded in or by the computer. The response is characterizable in nature. The characterizable nature of the response is analyzed in the computer to determine its nature. The nature of the response is categorized in the computer, preferably in accord with the conventional Glasgow Coma Scoring protocol. The computer produces or causes a stimulus to be produced dependent on the categorization of the response, such as a verbal cue or a pain stimulus.

The step of sensing a response from the patient comprises sensing an audio response by means of a microphone and/or sensing movement by at least one electrode. The movement is sensed by at least one electrode and comprises sensing eye movement of the patient and muscular movement of the patient.

When the response is an audio response from the patient it is analyzed to whether the audio response is a normal conversational response to a verbal cue, is a coherent response to a verbal cue, and/or is a recognizable word uttered by the patient in response to a verbal cue.

Where the response is a movement by the patient the response is analyzed to determine whether the movement is an eye opening or not in response to a stimulus, and whether the movement is a muscular or not in response to a stimulus. When the response is a muscular movement or not in response to a stimulus the analysis determines if it is in response to a pain stimulus and/or an appropriate movement or not to a verbal stimulus.

In the case of an appropriate movement in response to a pain stimulus the analysis determines by means of at least one body electrode if flexion is normal or rigid, and/or whether extension of a limb is normal.

The various advantages of the present invention will become apparent to one skilled in the art by reading the following specification and by reference to the following drawings wherein like elements are referenced by like numerals.

BRIEF DESCRIPTION OF THE DRAWINGS

FIG. 3a is a block diagram of the hardware components. FIG. 3b is a block diagram of the software modules.

FIGS. 5a–5d are diagrams of the time line of the AGCS algorithm as it is followed in four hypothetical subjects with conditions ranging from normal, through mild and severe head trauma to brain death.

Figure 1:
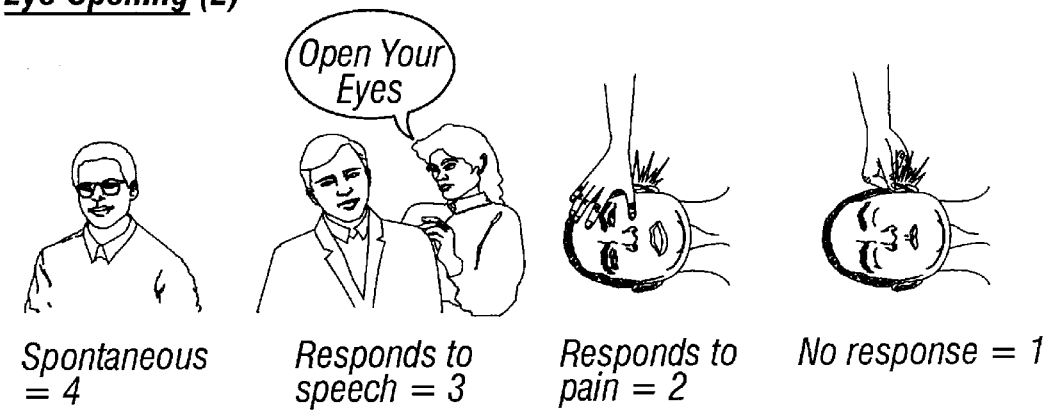
FIG. 1 is a cartoon of the prior art GCS assessment procedure as performed by nurses in hospitals around the world. It shows in a cartoon form the various eye, motor and verbal responses observed during GCS assessments.
Figure 1:
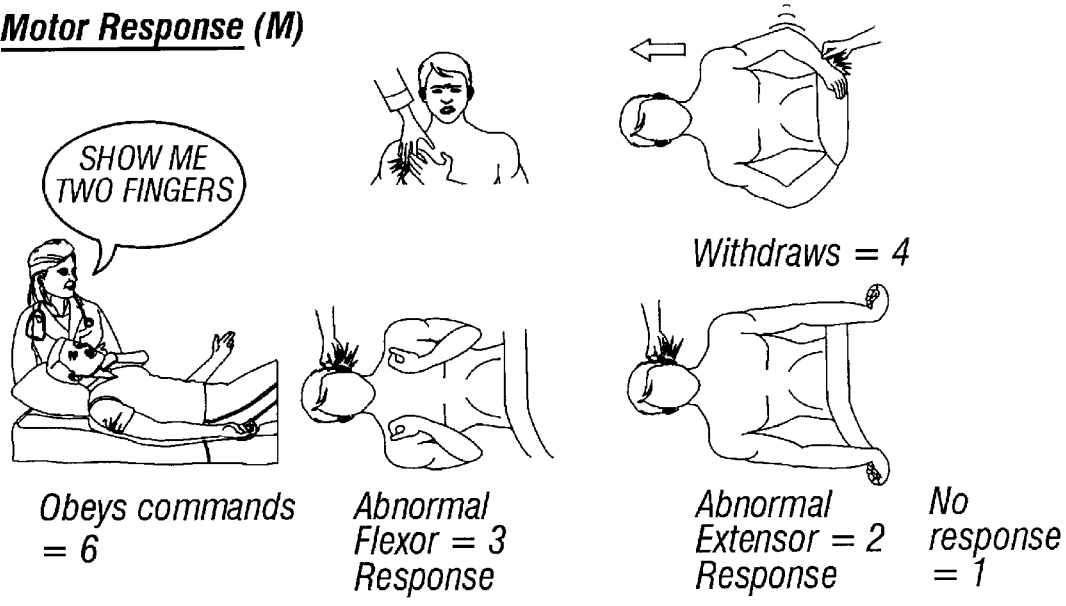
Figure 1:
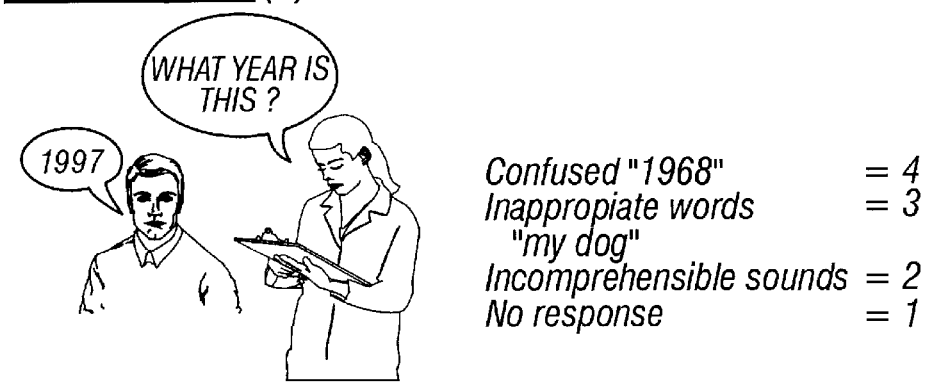

The invention now having been illustrated in the foregoing drawings, turn to the following detailed description of the preferred embodiments.

DETAILED DESCRIPTION OF THE PREFERRED EMBODIMENTS

A system and a method for computerized automated acquisition of the Glasgow Coma Score (GCS) is disclosed. In hospitals around the world the GCS is the most widely used scoring system for quantifying level of consciousness following traumatic brain injury. The Glasgow Coma Scale was first proposed by Teasdale and Jennett Teasdale et.al., "Assessment Of Coma And Impaired Consciousness: A Practical Scale" *Lancet* 2 81–4 (1974) and further elaborated (Avezaat et al 1977). Qualified personnel (e.g., nurses or physicians) commonly perform the assessment of the GCS of critically ill patients on a regular (hourly) basis. Changes in the GCS values are closely monitored by the critical care personnel and can often trigger additional tests such as CT scans, angiograms, etc. The automated AGCS system of the invention takes over the human assessors' task completely. Based on measurement of stimulus-induced standard physiological and verbal responses of the patient such as EMG, EOG and simple utterances, the system produces a coma score, which corresponds one-to-one with the score obtained by human assessors. This non-invasive technique allows frequent, pre-scheduled, objective, reliable and cost-effective estimation of the level of consciousness as represented by the GCS.

As described above GCS is comprised of three components, classified according to the type of response produced by the patient: eye (E); verbal (V); or motor (M). Of them, the motor response is the most important for patients who are in a coma or who have been intubated, which is the majority of ICU patients. In addition, the motor response is the easiest to elicit by verbal or pain stimulation. It can be recorded by standard EMG techniques, and its automated analysis is relatively straightforward. When eye and verbal responses are absent in patients with severely impaired consciousness, the motor response affords further differentiation of the level of consciousness Braakman "Inter Observer Agreement In The Assessment Of The Motor Response Of The Glasgow 'Coma' Scale" *Clin Neurol Neurosurg* 80 100–6 (1977). The eye responses are also relatively easy to record and analyze by means of EOG. Two pairs of standard EEG electrodes placed diagonally above and below the eyes can effectively capture both spontaneous and stimulus-evoked eye opening and closing. The verbal responses are the most difficult to score automatically as compared to the motor and eye responses. They require a speech recognition module, which has to function in relatively difficult ambient noise conditions. In designing the AGCS test we modeled the stimulus/response timing of both the examiner and the patient during the assessment process. For this purpose we studied a number of prerecorded GCS tests.

As stated above the AGCS method of the invention involves: (1) stimulation; (2) data acquisition before, during, and after the stimulation; and (3) on-line data analysis and automated data interpretation. The required stimuli are by nature verbal and pain. The verbal stimuli are delivered in the form of digitized sound from a soundboard. Versions of the verbal stimuli in various languages such as English, Spanish or other languages can be provided. The pain stimuli are produced by means of thermal or mechanical devices. The relevant response modalities are EOG, EMG (from both left and right hands flexors and extensors—a minimum of four electrodes). Described in more detail below are the stimulation, acquisition and analysis components of the AGCS method.

Figure 2:
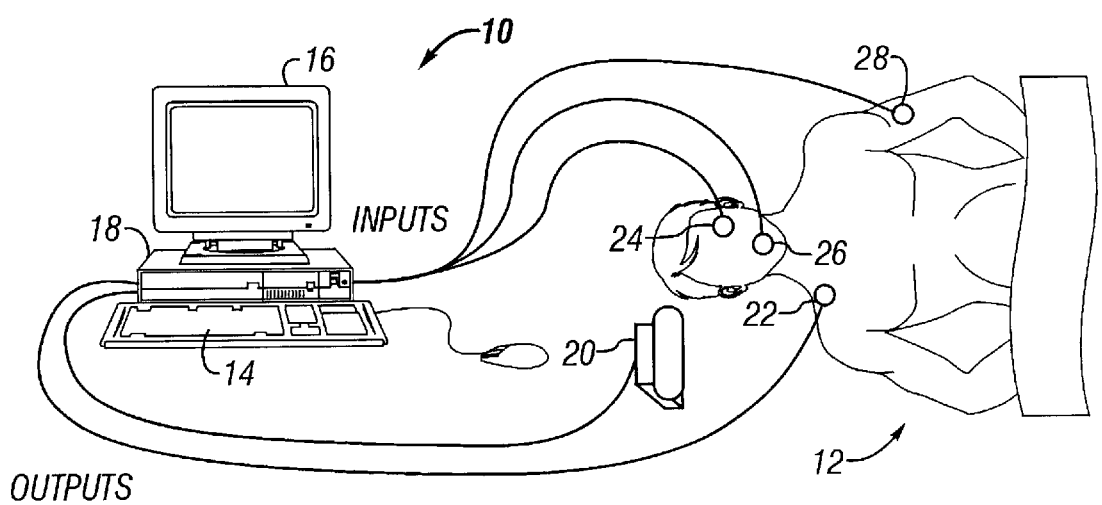
FIG. 2 is a diagrammatic depiction of the AGCS system of the invention as it is connected to a patient.

The basic hardware configuration of the invention is shown in FIG. 2. FIG. 2 is a diagrammatic depiction of the AGCS system 10 of the invention as it is connected to a patient 12. System 10 is controlled from a keyboard 14 and the Glasgow coma score is shown on a computer monitor 16, which is connected to a computer 18. The patient stimulators including a loudspeaker/earphone 20, and pain stimulating electrode 22 are attached to the patient as well as the data acquisition peripherals including EOG electrode(s) 24, EMG electrodes 28 and a microphone 26.

Figure 3A:
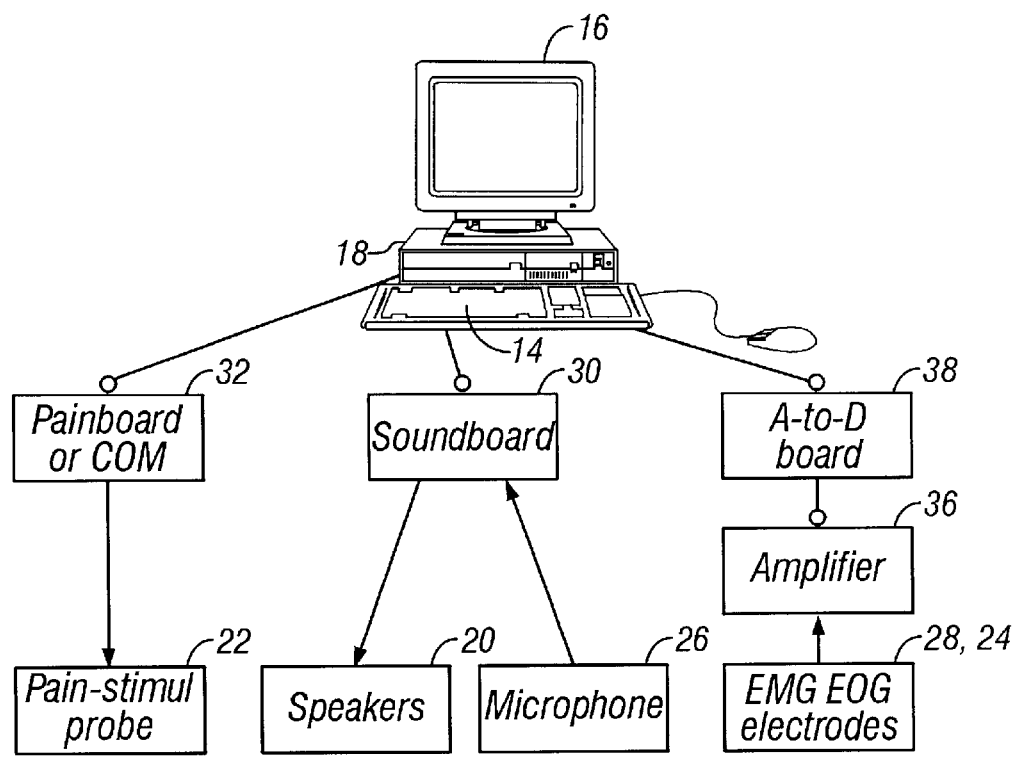
FIGS. 3a and 3b are block diagrams of the AGCS system in accordance with the present invention. In particular.
Figure 3B:
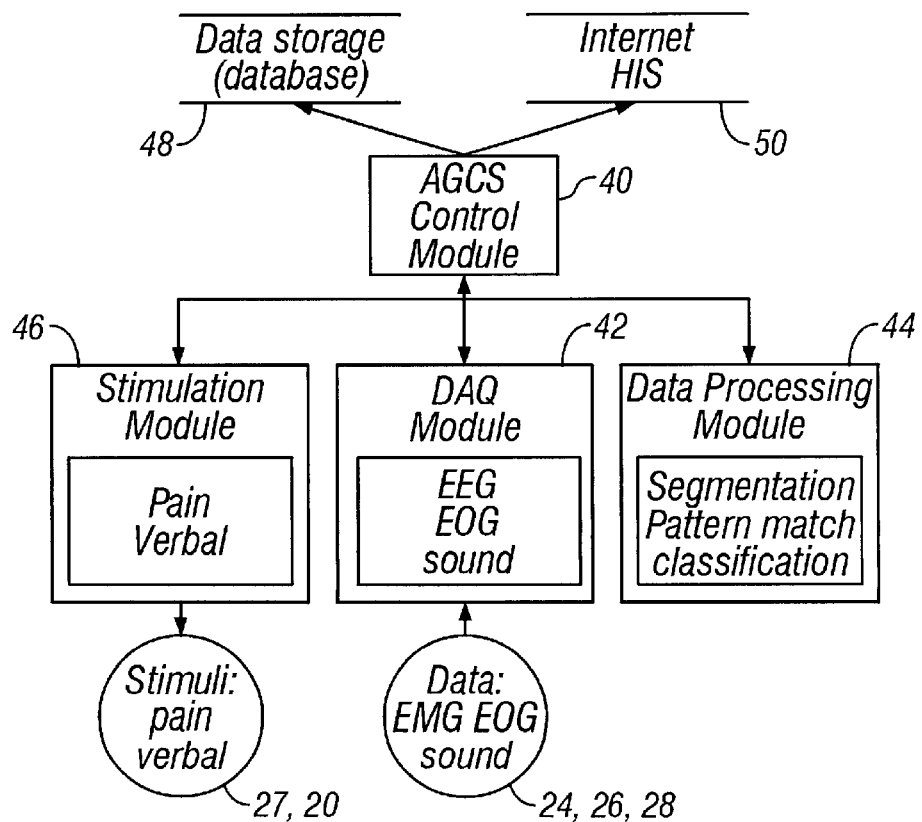

FIGS. 3a and 3b are block diagrams of the AGCS system in accordance with the present invention. In particular, FIG. 3a is a more detailed block diagram of the hardware components which include computer 18 equipped with display monitor 16 for control of the AGCS system 10 and visualization of the AGCS data. A soundboard 30 for generation of the verbal commands and digitization of the verbal responses, a pain-stimulation board or generic COM interface 32 for control of the pain stimulators 22, EEG/EOG/EMG amplifiers 36, and an A-to-D board 38 for collection and digitization of the EMG and EOG signals are coupled to computer 18. In addition, as described in FIG. 2 there are several data output peripherals such as: pain stimulators 22 (thermal or tactile) and verbal or audio stimulators 20 (speakers or earphones). Finally, as described in FIG. 2 there are data input probes including EOG and EMG electrodes 24 and 28 respectively and microphone 26.

FIG. 3b is a block diagram of the software modules including: AGCS control module 40, which implements the AGCS algorithm; data acquisition (DAQ) module 42 (EOG, EMG, sound); data processing module 44 for segmentation, pattern matching and classification of the input data; and stimulation control module 46, which controls the pain and verbal stimulators. In addition AGCS system 10 can include optionally a database 48 for storage of acquired GCS data and an interface 50 to the Hospital Information System (HIS) to download patient information and upload GCS scores as well as to the Internet to provide remote access to the data.

Consider first patient stimulation. The AGCS algorithm employs a response feedback mechanism to control the stimulation parameters such as stimulus duration and strength through module 46. The stimulation continues until: (1) the system 10 gets and recognizes the best desired response; or (2) until a preset time-out interval is reached. The patient 12 might need more or less stimulation to obtain his or her best response depending on the level of arousal at the time of the test.

Verbal stimulators are necessary to deliver the verbal commands such as "Open your eyes!" "Make a fist!" and "Lift your arm!". Loudspeakers and earphones 20 are the two standard options for delivery of verbal stimulation. For purpose of this invention, the use of loudspeakers 20 mounted on the bedside close to the patient's 12 head is more appropriate than the use of earphones, since it is desirable to minimize the number of items attached to the patient 12—especially to his or her head. At first glance it may appear that the loudspeakers 20 might bother other patients 12 in the same unit. In practice, however, the speakers 20 are not any more of a disturbance to the rest of the people in the ICU, than the other typical noises in an ICU or ER where there is no physical separation between the patient 12s' beds and sound travels freely. The speakers 20 are connected to soundboard 30 in personal computer 18, and the present invention is embodied in software of FIG. 3b to control the delivery of the sound and its loudness. Part of the content of the verbal stimuli (e.g. the patient's 12 name) can be prerecorded during the first session of GCS estimation, which the nurse has with the patient 12 upon his or her admission. Therefore, the verbal stimulation can be personalized. The battery of verbal (as well as any other stimuli) needs to be repeated while the expected responses are monitored through module 46 in order to obtain the best score. Fortunately, the common battery of verbal stimuli used for a standard GCS assessment is very limited. The content of the individual stimulation phrases and the content of the expected verbal responses are designed to discriminate between the various verbal scores.

Pain stimulators 22 are used to deliver painful (tactile) stimulation to the patient 12 in cases when he or she is not responding to verbal commands. There are a variety of potential pain stimulators 22 on the market. However, the pain stimulators 22 applicable to this invention are those that provide dynamic rather than tonic pain. In general, these stimulators 22 fall into three groups: (1) electrical; (2) thermal; and (3) mechanical. The electrical pain stimulators 22 are most widely used, but their usage for the purpose of this invention is not appropriate. The reason is a potential interference with other physiological monitoring devices and danger of passing electrical current to patients 12 with possible heart problems. Thus, the preferred choice is commercial thermal stimulators 22 capable of delivering temporal dynamic pain (e.g. the Thermal Pain Stimulator TRS-2001 by Medoc, Ltd. http://medoc-web.com/pain.html). These stimulators 22 can be finely controlled in terms of their intensity profile and duration by appropriate software. The pain-inducing electrodes/stimulators 22 are placed out of reach for the patient 12, and their use is minimized, so that the patient 12 does not remove them. Several pain-inducing stimulators 22 can be placed at different locations on the patient's 12 skin and they can be used alternately to avoid habituation.

The purpose of the data acquisition module 42 is to gather relevant responses from the recording electrodes 24 and 28 and microphone 26. It is important to note that responses can be produced with different intensities because ICU patients 12 often have a generalized weakness. In addition, the response reaction times can be severely impaired after traumatic brain injury and resulting treatments in the ICU. There are also patient-dependent constraints on the electrode placement, for which alternate electrode placement sites must be identified. Some examples of such conditions can be found in patients 12 who have large flaps of skin on their arms subsequent to profound weight loss, or in patients 12 with external head or body injuries that are in locations where the electrodes 24, 28 need to be placed.

The following types of responses are collected by the AGCS system 10. Consider first voice recordings. A highly sensitive directional microphone 26 records sounds produced by the patient 12, which are elicited by the verbal or pain stimulation. The voice is digitized by soundboard 30, stored in a file and made available to the voice recognition module 46 for on-line analysis.

The purpose of the EOG recording is to collect online signals, which are examined in real time by the analytical routines for evidence of spontaneous or stimulus evoked eye openings and closings. The following EOG setup works well for the purpose of the present invention: bipolar recordings, 1–10 Hz band-pass with a 60 Hz notch filter. With this setup the polarity of the signal deflection when the eyes open or close is easy to establish by means of visual inspection and can be detected by the computer. An alternate approach to recording the EOG for identification of eye opening/closing is to use infrared light reflective markers placed on the eye lids plus an opto-electronic camera for detection of eye movements. Problem arises in the situation when the patient 12 is covered or turned the wrong way, which makes the system 10 unusable.

The system 10 records EMG signals, which carry information about the activity of specific muscles commonly involved in producing the expected GCS motor responses. The information in these signals should be sufficient so that the proposed automated analysis routine can make correct categorization of the EMG responses with respect to the GCS scale. Therefore, the EMG recordings need to be set up so that they yield high signal to noise ratio with minimal distortion of the signal. The EMG signal is stochastic (random) in nature with an amplitude that ranges from 0 to 6 mV (peak-to-peak) or 0 to 1.5 mV (rms). It has usable energy limited to the 0 to 500 Hz frequency range, with the dominant energy being in the 50–150 Hz range. The muscle movements normally happen within 1,200 ms post stimulus presentation Konczak et.al. "The Development Of Goal-Directed Reaching In Infants: Learning To Produce Task-Adequate Patterns Of Joint Torque" *Exp Brain Res* 113 465–74 (1997).

The preferred embodiment uses the following EMG parameters:

(1) EMG sampling rate 500 Hz.

(2) Use of standard silver chloride surface electrodes 28 with 5 mm diameter.

(3) EMG electrodes 28 are placed on the respective muscles to minimize possibility of cross talk.

(4) The earlobes A1 and A2 are tied together with the COM input.

(5) Montage settings: Notch filter=ON; sensitivity=50; LF=10; HF=100;

(6) All EMG signals are digitized online (12-bit).

The recordings produced by the AGCS system 10 attempt to reduce the noise generated by sources such as: (1) inherent noise in the detection and recording equipment; (2) ambient noise from external sources of electromagnetic (EM) radiation; and (3) motion artifacts in the range from 0 to 20 Hz originating from poor interface between electrodes and the skin and from cable movement. The AGCS system 10 uses the minimum number of EMG electrodes 28 that give sufficient information. In order to minimize the number of electrodes the system 10 uses motor actions, which are equivalent in terms of response to the standard GCS-M actions expected. For instance, instead of asking the patient 12 to "Show two fingers", which elicits a response the correctness of which is difficult to recognize without highly sophisticated (and generally unreliable) image analysis, the present system 10 asks him or her to "Make a fist" and monitors the EMG of the muscles involved.

In the present system 10 EMG is recorded from the flexors (biceps—elbow flexor, brachioradialis—forearm flexor; anterior deltoid—flexor initiates flexion at the shoulder joint) and extensors (triceps—elbow extensor; anconeus muscle—other elbow extensor) of both hands (Konczak et al 1997). EMG electrode pairs 28 are placed on top of the muscles to produce higher quality EMG signal with less ECG signal interference and external noise as compared to electrodes 28 referenced to electrically silent parts of the body such as the nose, earlobes or the mastoid bone. In order to optimize the number of muscle fibers from which the recording is made the system 10 uses bar-shaped electrode pairs (each 1-cm in length and 2 mm in width) placed along the longitudinal midline of the muscle between two motor points. Also used is differential detection and amplification with high common mode rejection ratio (CMRR about 90 dB). To prevent signal attenuation and distortion, differential amplifiers with high input impedance (about 10 megaohms in parallel with 5 picoFarads) are used.

Standardization in terms of muscle response systems can be developed to render the system 10 immune to possible trauma in the arm. The recorded muscle responses are simple to detect automatically and, if needed, the AGCS system 10 can be configured at the time of setup so that instead of recording EMG from arms it will record from legs, etc. A list of alternative sites for recordings can be developed so that one can make such standardization possible and practical. In practice, during the system 10 setup the technician needs to exclude the injury-influenced muscle groups and replace them with alternate sites. The system 10 is sufficiently flexible, so that it models/mimics the assessment profile, which a trained practitioner uses typically. This was achieved by closely observing and formalizing the practitioner's decision process while he or she is running the GCS test as reflected in FIG. 4—the AGCS algorithm.

The objectives of the automated data analyses are: (1) to recognize/classify the verbal responses of the patient 12; (2) to recognize eye openings from measured EOG; and (2) to recognize correct arm/leg movement as well as flexion and extension movements of the limbs from EMG. The three essential components of the overall analyses are discussed in detail below.

Consider first verbal analyses. The objective of verbal data analysis is to interpret and classify the verbal responses of the patient 12 if there are such responses. This is the most difficult task as compared to the eye and motor modalities, because it requires automated speech recognition in a difficult environment. This environment includes a sick patient 12, who might give unintelligible responses that are often difficult even for the nurse or a relative to understand, and an often noisy ICU room. In addition, patients 12 can be speaking different languages. Also, patients 12 can have severe accent or trauma-related obstructions of their speech. Fortunately, the verbal response domain is very limited since the system 10 is attempting to recognize the responses to a very short list of standard questions. To accomplish this analytical task cost-effectively, the system 10 uses technology that can recognize single words or phrases. Some commercial PC-based software packages are already available on the market (e.g. the Dragon software, or the IBM voice recognition package are some of the best). Such packages can be used and/or incorporated in the AGCS system 10. However, even if the AGCS system 10 does not contain a verbal recognition module 46, it has been demonstrated, Meredith et.al. "The Conundrum Of The Glasgow Coma Scale In Intubated Patients: A Linear Regression Prediction Of The Glasgow Verbal Score From The Glasgow Eye And Motor Scores [In Process Citation]" *J Trauma* 44 839–44; discussion 844–5 (1998) that in intubated patients 12, a linear regression on the Glasgow Eye and Motor can predict the Glasgow Verbal Score.

Consider now EOG analyses. The purpose of an EOG analysis is to recognize if the patient 12 is opening his or her eyes spontaneously or in response to stimulation. This is a relatively simple task, since a pair of EOG electrodes placed diagonally above and below the eye is sufficient. The system 10 recognizes eye blinks as well as when the subject opens and closes his or her eyes by the direction of signal displacement on the recording. Eyes openings and closings have the same base line if filters are set appropriately. A simple amplitude threshold mechanism is used to analyze the EOG response. In situations when this is not sufficient, the system 10 applies more sophisticated and robust methods. One such method is based on calculations of the zero crossing complexity of the EOG signals measured before during and after eye movements. A difference measure index (DM) is used for this purpose. For the purpose of this invention, this algorithm works very well. Even at the worst case which we examined (response time=1s, delay time= 0.5s, step=0.0625s), the DM was still much bigger than the corresponding t-value at significant level of 0.01. This means that even at such a short time the eye movement response to stimulus can be successfully detected by this method.

Automated analysis and interpretation of the EMG signals are the core of the AGCS system 10. For decades the preferred manner for processing EMG signals was to calculate the integrated rectified signal over specified intervals of time and to form time series of integrated values. However, the root-mean-square (rms) measure has proven to be a more appropriate since it provides a physically meaningful measure of the power of the signal. The AGCS system 10 uses a maximal likelihood method (MLM) classifier of the type proposed by Wen-Juh et.al., "The Application Of Cepstral Coefficients And Maximum Likelihood Method In Emg Pattern Recognition (Movements Classification)" *IEEE Transactions on Biomedical Engineering* 42 777–85 (1995). However, different methods for analysis of the EMG data can also be used. Which one of these methods is the most effective in mapping the EMG signals to the motor component of the GCS depends on the particular patient 12 case. Listed below are several of the methods that can be used by the AGCS system 10 for EMG data preprocessing.

One option Konczak et.al. "The Development Of Goal-Directed Reaching In Infants: Hand Trajectory Formation And Joint Torque Control" *Exp Brain Res* 106 156–68 (1995) is to filter the EMG signals with a 3- to 100-Hz band-pass filter for the total trial duration. Further, the signals can be rectified and smoothed with a 21-point moving-average filter. Another option is to pass the recorded EMG signals through several filters and to select the one with the best discriminative power with respect to the GCS-M. Then, search for different patterns of EMG activation of the flexor/extensor pairs such as (a) reciprocal innervation, (b) co-activation. Examples of the expected EMG patterns can be found in (Konczak et al 1997). Yet another analytical option can be adapted from Fellows as reported in Fellows et.al. "Agonist And Antagonist Emg Activation During Isometric Torque Development At The Elbow In Spastic Hemiparesis" *Electroencephalogr Clin Neurophysiol* 93 106–12 (1994). He uses EMG channel ratios (percentages) for flexor/extensor signals.

An important issue in the EMG analysis is how to interpret "complex" multi-channel responses if the number of EMG electrodes 28 and positions is not sufficient. Some of the pertinent algorithms for pattern analysis are: (1) space-time clusters of EMG data or identification of sharp signal swings in both EMG and EOG data; (2) classical signal integration methods combined with threshold cutoff filtering; (3) fuzzy set pattern recognition (FSPR) and hidden process modeling techniques. FSPR has been successfully used to characterize complex dynamic processes in EEG signals recorded in the states of wakefulness or drowsiness and can be modified for the purposes of AGCS Gorek et.al. "Electromyograms In Erectile Dysfunction And Computer-Assisted Interpretation" *Biomed Tech (Berl)* 42 48–54 (1997a); Gorek et.al. "Computer-Assisted Interpretation Of Electromyograms Of Corpora Cavernosa Using Fuzzy Logic" *World J Urol* 15 65–70 (1997b); Guiheneuc et.al. "Signal Processing In Electromyography: A Review" *Neurophysiol Clin* 27 445–70 (1997); Wallner, "Detection Of Rapid Eye Movement With Rapidly Adapting Neuronal Fuzzy Systems In Imprecise Rem Syntax" *Biomed Tech (Berl)* 41 84–90 (1996) and (4) artificial neural network (ANN) approaches, which have been shown to provide significant robustness in automated processing of complex, degraded, noisy and unstable EMG signals Hassoun et.al. "Nnerve: Neural Network Extraction Of Repetitive Vectors For Electromyography—Part I: Algorithm" *IEEE Trans Biomed Eng* 41 1039–52 (1994a); Hassoun et.al. "Nnerve: Neural Network Extraction Of Repetitive Vectors For Electromyography—Part II: Performance Analysis" *IEEE Trans Biomed Eng* 41 1053–61 (1994b).

The use of artificial neural networks (ANN) in classifying electromyographic (EMG) data trained with the momentum back propagation algorithm has recently been demonstrated. In a recent study, Schizas et.al. "Learning Systems In Biosignal Analysis" *Biosystems* 41 105–25 (1997), the self-organizing feature map algorithm, the genetics-based machine learning (GBML) paradigm, and the K-means nearest neighbor clustering algorithm were applied and compared on the same data set.

Surface EMG pattern classification has been used in artificial limb control Doerschuk et.al. "Upper Extremity Limb Function Discrimination Using Emg Signal Analysis" *IEEE Transactions on Biomedical Engineering* BME-30 18–29 (1983); Ito et.al. "Emg Pattern Classification For A Prosthetic Forearm With Three Degrees Of Freedom", pp 69–74 (1992); Jangrvoo et.al. "Hybrid Hmm-Mlp Classifier For Prosthetic Arm Control Purpose", pp 21–4 vol.1 (1996); Lee et.al. "The Control Of A Prosthetic Arm By Emg Pattern Recognition" IEEE *transactions on automatic control* ac-29 290–302 (1984); Saridis et.al. "Emg Pattern Analysis And Classification For A Prosthetic Arm" *IEEE Transactions on Biomedical Engineering* BME-29 403–12 (1982) and functional electrical stimulation Graupe, "EMG pattern analysis for patient 12-responsive control of FES in paraplegics for walker-supported walking" *IEEE Transactions on Biomedical Engineering* 36 711–19 (1989); Kocyigit et.al. "Emg Pattern Discrimination For Patient-Response Control Of Fes In Paraplegics For Walker Supported Using Artificial Neural Network (Ann)", Eds et.al. pp 1439 –41 vol.3 (1996). These applications provide good precedents for the automated assessment of the GCS motor score. Among the many classifier schemes reported in the above applications, the combination of cepstral coefficients as features with the MLM classifier is an effective and simple method (Wen-Juh et al 1995). Cepstral coefficients have been widely used as a good classification index of EMG, Sang-Hui et.al. "Emg Pattern Recognition Based On Artificial Intelligence Techniques" *IEEE Transactions on Rehabilitation Engineering* 6 400–5 (1998) Silvestro et.al. "A Hybrid Approach To Emg Pattern Analysis For Classification Of Arm Movements Using Statistical And Fuzzy Techniques" *Medical Engineering & Physics* 21 303–311 (1999) and have been shown to have better discriminative power than Auto Regressive (AR) coefficients (Wen-Juh et al 1995). Compared with other statistical classifiers such as the Euclidean distance measure (EDM) and the weighted distance measure (WDM), MLM makes fewer assumptions about the unknown statistical properties of the EMG signals. Therefore, it is closer to the optimal Bayes classifier and exhibits better performance. The AGCS employs two improvements, Xiao H, et.al., "Multivariate AR Modeling Of Emg For The Classification Of Upper Limb Movements" *Medical Engineering and Physics* (submitted) (2000), of the basic classification scheme used in (Wen-Juh et al 1995). One-shot classifications are most desirable in situations such as GCS motor scoring when measurements can not be repeated many times.

Algorithms for EMG noise-reduction play a major role in achieving such a goal. AGCS uses a method of surrogate averaging, Xiao H, et.al. "Improved Classification Of Multi-Movement Emg Using Surrogate Data Averaging" *Clinical Neurology* (submitted) (1999). The actual averaging is implemented in feature space among the features of original single measurement as well as several realizations of surrogate data. Such surrogate data has been widely used in the nonlinear analysis of EEG signals. For instance, it is used for testing of the hypothesis that EEG can not be distinguished from linear stochastic signals that may be measured through a static nonlinear measurement function Theiler et.al. "Testing For Nonlinearity In Time Series: The Method Of Surrogate Data", pp 77–94 (1992). To generate such surrogate data AGCS uses an advanced algorithm, Schreiber et.al. "Improved Surrogate Data For Nonlinearity Tests" *Physical Review Letters* 77 635–8 (1996), that can be iterated to get a finer match of the spectrum between original and surrogate data.

The issue of artifact identification and rejection is an important one, since a variety of different types of artifacts come into play. For instance, there are movement artifacts (these are slower than EMG and can be filtered out), Artifacts due to bad electrodes (automatic electrode impedance testing before ACGS can eliminate these), etc.

Figure 4A:
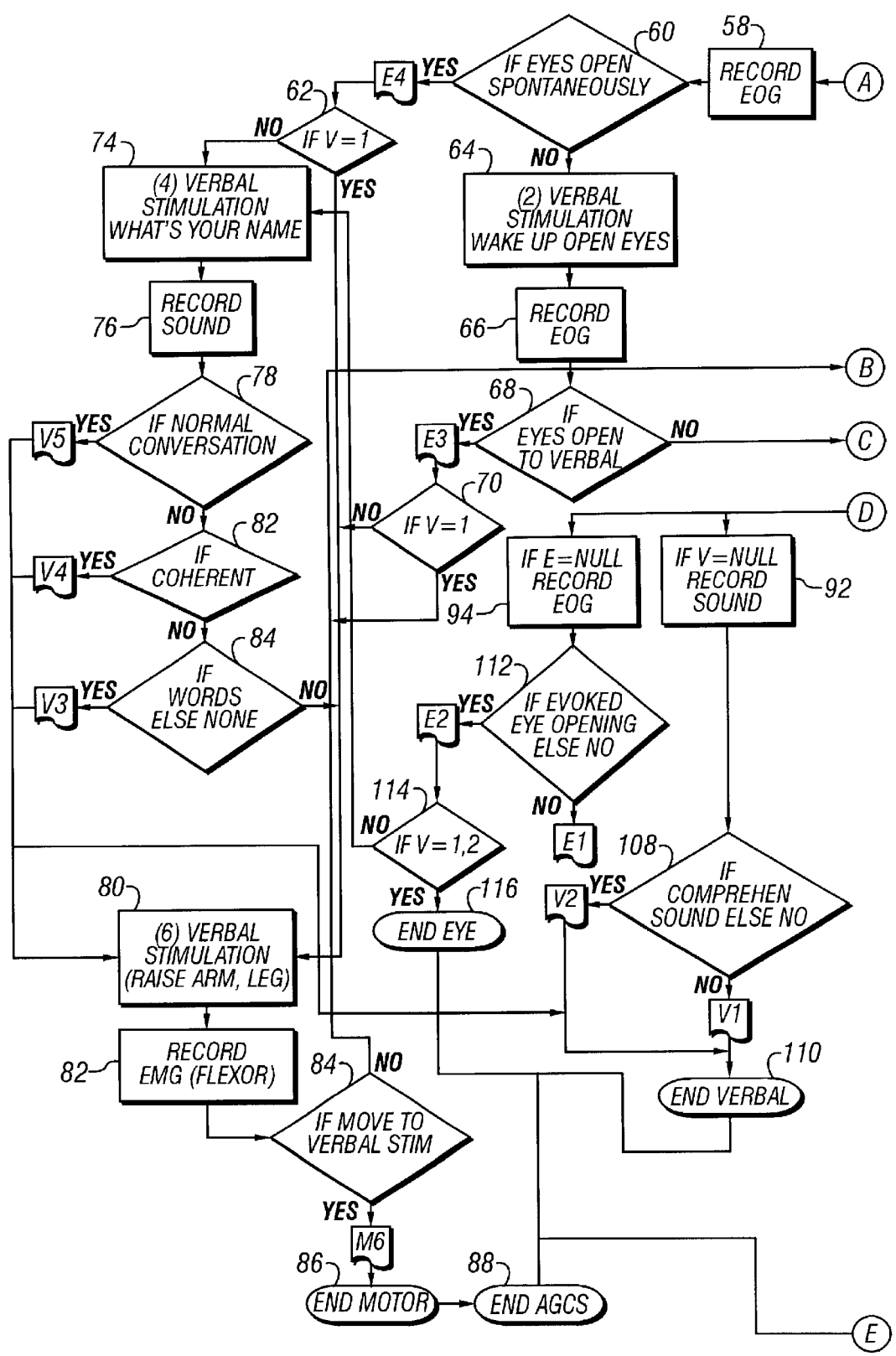
FIG. 4 is a flowchart or decision tree of the AGCS algorithm in accordance with the present invention.
Figure 4B:
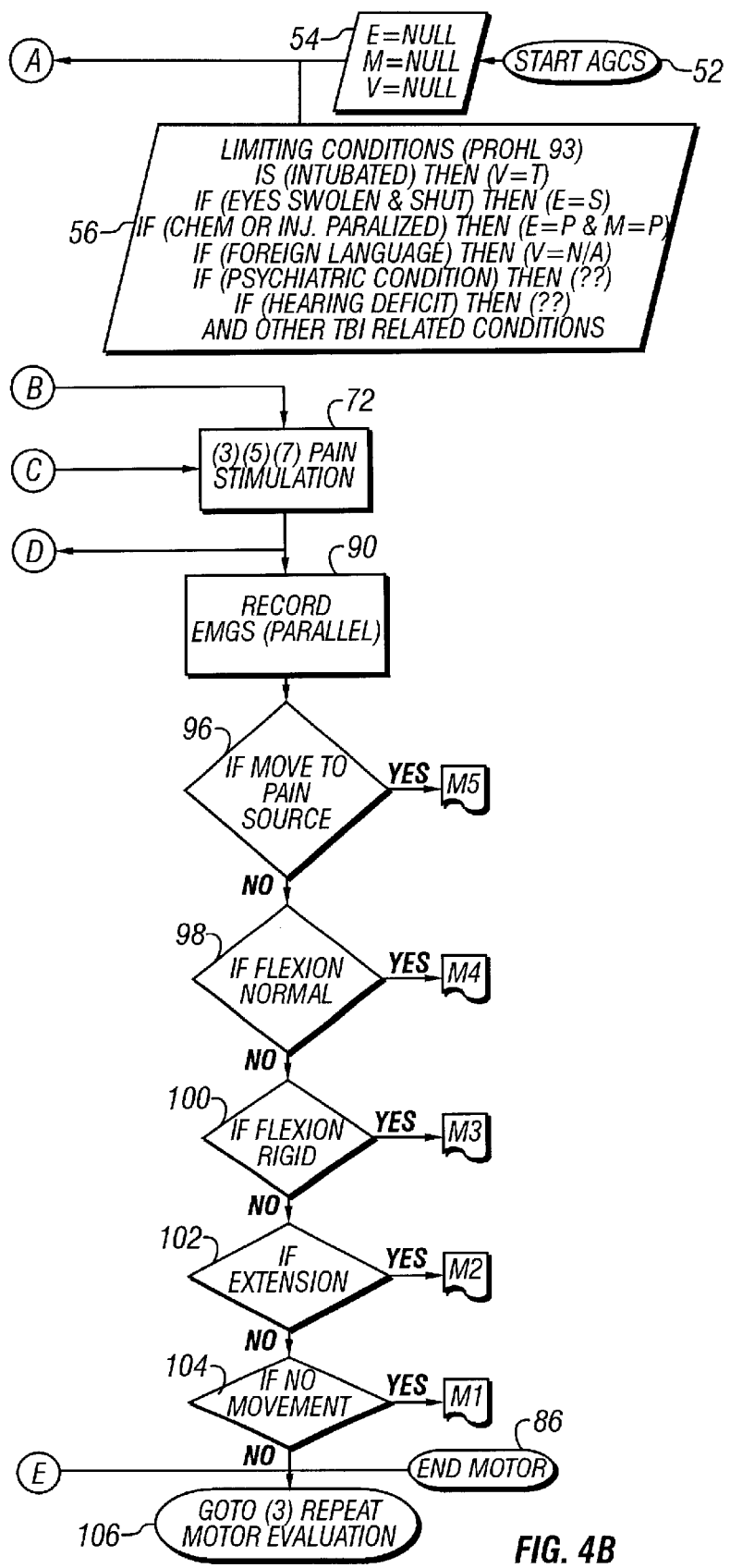

The AGCS algorithm of the invention is shown as a flowchart in FIG. 4. Each step in the flowchart is automatically repeated a number of times until the best response is obtained or until the AGCS algorithm is unsure about the response (questionable). For example, both left and right side EOG and EMG are recorded to find the best response. To read and interpret the flowchart, start at the top right-hand corner and follow the arrows while making decisions depending on the patient's response. The system traverses the decision tree according to the patient responses entering repeated cycles or loops of stimulation→recording→analysis→categorization. The cycles repeat until it reaches a single end-node in each of the three branches of the tree (verbal, motor and eye). The trauma classifications are GCS<8 is severe, 9<GCS<12 is moderate, and GCS>12 is mild.

The method starts at step 52 in FIG. 4. The E, M, and V values are initialized to zero at step 54. Depending on the patient's condition certain limiting conditions are entered at step 56, such as whether patient 12 is intubated (V=T), whether the eyes are swollen shut or otherwise impaired (E=S), if paralyzed by any means (E=P, M=P), if language specific (V=N/A), if subject to a psychiatric state or disorder (V=N); if hearing impaired for any reason (V=D) and any other conditions which may affect the test. An EOG is recorded at step 58. A determination then made whether the eyes are spontaneously open or shut at step 60. If the eyes are spontaneously open, E is set to 4 and the value of V is tested at step 62. Otherwise verbal stimulus is provided asking patient 12 to open his eyes at step 64. Another EOG reading is then made at step 66. If the eyes are then opened as determined at step 68, E is set to 3 and the value of V is tested at step 70. Otherwise pain stimulus is then produced at step 72. If at step 70 V=1 then the method branches to step 80 described below. If at step 70 V≠1 then the method branches to step 74 described below.

If at step 60 the eyes are spontaneously open and V≠1 at step 62, then patient 12 is verbally asked "What's your name?" at step 74. Otherwise the method branches to step 80 described below. Any sound made by patient 12 in response is recorded at step 76. If the response is determined to be a normal conversational response at step 78, then V is set to 5, the verbal test is terminated at step 110, and another verbal cue is provided at step 80 to make a movement of some type, e.g. "Raise your arm" etc. If the response made by patient 12 in response as recorded at step 76 is not normal conversation as determined at step 78, then a determination is made at step 80 whether the abnormal conversation is coherent or not at step 82. If the response is coherent, then V is set to 4, the verbal test is terminated at step 110, and the method goes to step 80. If the abnormal conversation is incoherent, then the method determines at step 84 if recognizable words were spoken. If recognizable words were spoken, then V is set to 3, the verbal test is terminated at step 110, and the method goes to step 80. Otherwise, the method branches to step 72 to produce pain stimulus.

After the verbal command to move a limb at step 80 is given, an EMG recording is made at step 82. If appropriate movement is detected at step 84 then M is set to 6, the end of motor testing is reached at step 86, and the end of the AGCS method at step 88.

After pain stimulus is provided at step 72 EMG is recorded at step 90 in parallel with recording of sound at step 92, and eye opening at step 94. If there is movement in response to the pain stimulus as determined at step 96, then M is set equal to 5 and the motor testing is exited at step 86 and the AGCS method at step 88. If there is no movement then flexion is determined at step 98. If flexion is normal, then M is set to 4 and the motor testing is exited at step 86 and the AGCS method at step 88. If flexion is not normal, then it is determined at step 100 whether flexion is rigid. If flexion is rigid, then M is set to 3 and the motor testing is exited at step 86 and the AGCS method at step 88. If flexion is not rigid, then a determination is made at step 102 if normal extension exists. If there is normal extension, then M is set to 2 and the motor testing is exited at step 86 and the AGCS method at step 88. If there is abnormal extension, then a determination is made at step 104 if there was movement. If there was no movement as determined at step 104, then M is set to 1 and the motor testing is exited at step 86 and the AGCS method at step 88. If there was movement, then the motor evaluation is repeated at step 106 by return to step 72 and a repeated application of a pain stimulus. The cycles through the flow diagram of FIG. 4 continues until step 88 is reached.

At step 92 sound is recorded if V=0. If the recorded sound is incomprehensible as determined at step 108 then V is set to 2 and the end of the verbal routine is reached at step 110. If there is no recorded sound as determined at step 108 then V is set to 1 and the end of the verbal routine is reached at step 110.

If E=0 at the EOG recording of step 94, and if the eyes are opened on the pain stimulus as determined at step 112, E is set to 2, otherwise E is set to 1. A determination is then made at step 114 if V is 1 or 2. If neither, then the method branches to step 74. If V is 1 or 2, then the end of the eye test is reached at step 116 and of the AGCS test at step 88.

Scheduling of AGCS acquisition sessions is software settable (e.g., every 15 min, 30 min, or whatever). AGCS may take less time to measure as compared to the standard GCS. This is because in AGCS most recordings/analyses steps can be done in parallel while the human expert (especially the less trained), will do them in a serial fashion while repeating stimulations to reach each leaf of the decision tree.

Four hypothetical examples of the manner in which the AGCS algorithm of FIG. 4 is executed in patients 12 ranging from normal, through mild and severe head trauma to brain death are demonstrated graphically in FIGS. 5a–5d. FIGS. 5a–5d are diagrams of the time line of the AGCS algorithm as it is followed in four hypothetical patients 12 with conditions ranging from normal, through mild and severe head trauma to brain death. Each patient 12 is subjected to three or more repetitions of the "stimulate, record, analyze and categorize cycle" shown on the X-axis. Shown on the Y-axes are the types of stimulations and recordings in the AGCS algorithm. Which of the available stimuli and recording modalities are used in each case depends on the severity of the injury.

In FIG. 5a in cycle 1 a normal subject or patient 12 is tested. An EOG recording is made and since patient 12 spontaneously opened his eyes as determined at step 60, E is assigned a value of 4. In cycle 2 verbal stimulus is applied at step 74 and a normal conversational response is obtained at step 78, so that V is assigned a value of 5. In cycle 3 a verbal request is made to move a limb at step 80 which is successfully performed so that M is assigned a value of 6 at step 84. The total AGCS for a normal patient or subject is 15.

In FIG. 5b a patient 12 with mild head trauma is tested. In cycle 1 there is no spontaneous opening of the eyes at step 60. Verbal stimulus is then applied in cycle 2 at step 64 and patient 12 opens his eyes as determined at step 68. E is assigned a value of 3. Verbal stimulus is then applied in cycle 3 as determined in steps 70 and 74 and patient 12 responds in abnormal conversation but coherently at step 82. V is assigned a value of 4. A verbal command to move is given at step 80 in cycle 4 and patient 12 makes an appropriate responsive movement at step 84 so that M is assigned a value of 6. The total AGCS for a mild head trauma patient is more than 8, namely 13 for this hypothetical patient.

In FIG. 5c a patient 12 with severe head trauma is tested. In cycle 1 there is no spontaneous opening of the eyes at step 60. Verbal stimulus is then applied in cycle 2 at step 64 and patient 12 fails to open his eyes as determined at step 68. Pain stimulus is applied in cycle 3 at step 72. Pain stimulation will be provided if $E \leq 2$, $V \leq 2$ or $M \leq 5$. The patient's eyes open so that E is assigned a value of 2. The patient makes an incomprehensible sound at step 108 so that V is assigned a value of 2. The patient's flexion is rigid, so that M is assigned a value of 3. The total AGCS for a severe head trauma patient is less than 8, namely 7 for this hypothetical patient.

In FIG. 5d a patient 12 who is brain dead is tested. In cycle 1 there is no spontaneous opening of the eyes at step 60. Verbal stimulus is then applied in cycle 2 at step 64 and patient 12 fails to open his eyes as determined at step 68. Pain stimulus is applied in cycle 3 at step 72. The patient's eyes do not open so that E is assigned a value of 1. The patient makes no sound at step 108 so that V is assigned a value of 1. The patient's makes no movement, so that M is assigned a value of 1. The total AGCS for a brain death head trauma patient is 3.

There are a number of external factors that may affect the patient's 12 level of consciousness and may alter the GCS independently of the brain injury. These factors (to the extent that they are known) are taken into account and incorporated into the AGCS method. In practice, prior to running the actual AGCS application, these factors are entered in the AGCS system 10 through a graphical user interface (GUI), which consists of check-boxes, pull-down menus and text fields. The effect of these factors on the GCS is interwoven with the logic of the AGCS algorithm. Among those external factors are: (1) a patient state of shock; (2) hypoxemia; (3) drug use (pharmacologically relaxed); (4) alcohol intoxication; (5) metabolic disturbances and others. Additional factors can be incorporated as they are identified.

Besides the aforementioned factors, there are other factors that might interfere with the procedure of GCS estimation that are taken into account, including:

(1) Spinal cord injury,—such condition makes the motor scale invalid (N/A M of upper limbs)

(2) Severe orbital trauma,—this condition makes eye opening impossible to assess. (N/A E).

(3) Endotracheal tube in place (intubated—T)—patients 12 cannot talk. (N/A V-E#, Vintubated, M#) or GCS+T.

(4) Pharmacologically paralyzed patient 12, Offner et.al. "Revision Of Triss For Intubated Patients" *J Trauma* 32 32–5 (1992)—valid GCS can NOT be obtained.

(5) Age factor—the GCS also has limited utility in children, particularly in those younger than 36 months.

The AGCS system 10 can be used in critical care units, intensive care units, recovery rooms, emergency rooms and indeed all locations where GCS is regularly assessed (i.e., anywhere that there are patients with impaired consciousness). Most of these environments currently have computerized monitoring infrastructures.

A computer equipped with specialized hardware shown in FIG. 3a runs the AGCS software as depicted in FIG. 3B. To the technologist who is setting up patient 12, AGCS system 10 shown diagrammatically in FIG. 2 appears as a computer with several input lines (EEG, EMG, microphone 26) and several output lines (speakers 20 and pain stimulators 22), which he or she attaches to the patient 12. The process of patient setup, which is done once upon admission of the patient to the unit, resembles the standard setup of patients 12 for EEG or sleep study.

The AGCS software is comprised of three basic modules: (1) Analysis control module 40, (2) Stimulation module 46 and (3) Acquisition module 42. The stimulation module 46 is attached by means of wires to stimulation devices including pain stimulator(s) and verbal stimulator(s). The acquisition module 42 is attached to a set of probes including a microphone 26, and some EOG and EMG electrodes 28.

There are at least three possible ways of reducing the invention to a practical clinical device:

1. AGCS can be an add-on module to EEG monitoring equipment: Traditional EEG companies like Nicolet Biomedical, Biologic, Grass, Telefactor, NCI, etc. offer a variety of neuro-monitors for ICU use. Most of the existing systems on the market contain auditory, optical and electrical stimulators 22 (for electrophysiology recordings: brainstem auditory evoked potentials (BAEP), visual evoked potentials (VEP), somatosensory evoked potentials (SSEP) along with the EEG recording amplifiers. Therefore, potentially all of the existing stimulation and recording hardware can be used for the AGCS purposes without the need of incorporating additional hardware, since EEG amplifiers can also be used for EMG/EOG measures. Some of these systems are also based on off-the-shelf computer platforms and have built-in sound boards and come with speakers 20 and microphones 26. The availability of such hardware components reduces AGCS system 10 to a purely functional (software) extension to existing monitors, which substantially reduces its price.

2. AGCS can be supplied as an add-on to vital signs monitoring equipment. Most contemporary hospitals and their ICUs are equipped with vital signs monitors manufactured by a number of companies such as Marquette Electronics, Space Labs, HP, Datex (in Europe). There is a huge installed base of such equipment. One general problem with the installed instrument base, however is that the commonly used vital sign monitors are not usually equipped with EMG and EOG/EEG acquisition modules 42 and often lack stimulators 22.

Nevertheless, some of them, especially the new generation of Windows NT based monitors, can be potentially modified to allow for automated GCS assessment.

3. System 10 can be provided as a stand-alone hardware/software AGCS system 10, such as an AGCS system 10 which is based on off-the-shelf components such as computer, data acquisition board, stimulator boards and the AGCS software package, which will control all of the above. System 10 could be loosely or closely integrated with the existing vital-signs and EEG monitors.

In a recent study (Xiao and Nenov 1999) data collected by the AGCS/EMG method was subjected to two different assessments of its classification accuracy. In a within-subject classification, the classification was carried out for each subject by processing the feature vectors obtained from that subject. In an inter-subject classification, the accuracy was judged by considering all feature vectors obtained from all subjects together. In both cases, the leave-one-out method was implemented to evaluate the classification accuracy. Using these classification techniques, we achieved 95 to 100% accuracy in classification of the following four upper-limb movements: elbow flexion (EF), elbow extension (EE), internal elbow rotation (ER) and internal shoulder rotation (SR). GCS motor responses from M=5 to M=2 may involve one or more of these four upper limb movements in combination.

The reliability of AGCS assessment, in terms of the number of generated false positive and negative classifications (mappings to the standard GCS), depends on: (1) the integrity of the electrodes and correct location for both stimulation and recording electrodes; (2) the sensitivity of the recognition algorithms; and (3) the precision of the temporal modeling of the GCS exam. In other words, how close the duration of the individual steps of the AGCS corresponds to the duration of the steps taken by a human examiner. These time intervals are determined by the ability of patient 12 to respond within certain physiologically appropriate and expected time windows. The term "false positive" refers to the case of a system mistakenly detecting a change in the GCS while there is actually no change. The term "false negative" describes the case in which a true change of the GCS goes undetected by the AGCS system 10. Systems that have a low rate of false positives are called "specific", while those with a low rate of false negatives are referred to as "sensitive".

To classify the performance of the AGCS algorithm/system 10 as correct, we have developed appropriate criteria for accuracy of classification. While comparing the consistency between two raters of GCS, the real question was if the AGCS is any less reliable than another human rater. To test this, we asked two human raters to blindly rate the same patients who were studied with the AGCS. In a study aimed to compare the GCS scoring consistency, Ellis as reported at Ellis et.al. "Aspects Of Neurosurgical Assessment Using The Glasgow Coma Scale" *Intensive Crit Care Nurs* 8 94–9 (1992), videotaped multiple GCS sessions. In situations when the AGCS does not have sufficient information to generate an output we can include an outcome in the AGCS decision tree that says "outcome ambiguous—operator intervention needed".

The AGCS method is minimally invasive. The number of stimulators 22 and probes used in this invention are minimal and optimal, which is assured by using some of the probes for more than one purpose. If the patient 12 is not awake in the beginning of the AGCS session, it is necessary to wake him or her up by electronic means. Of course, there are many ways to achieve this. In the preferred embodiment, we prefer to alternate various methods so that patient 12 does not get annoyed or desensitized. In developing the AGCS system 10 we considered a number of human factors. For instance, what if patient 12 becomes annoyed or irritated by multiple AGCS sessions and pulls off the stimulating electrodes? Perhaps the best way to avoid this situation is to provide feedback from the analyzed patient 12 response to the stimulators 22, e.g., shut the stimulators 22 off if they are not necessary or if the expected response has been received or if a preset time-out window expires.

The AGCS method has many advantages compared to the classical GCS method.

(1) It does not introduce subjective bias based upon previous assessments, as may commonly occur when nurses and physicians assess the GCS. For instance, the AGCS algorithm automatically double-checks when it gets a level that is more than 1 level different from the previous measurement in either the eye or the motor score. However, a bias could be deliberately introduced into the AGCS if it is demonstrated through clinical trials that it will be beneficial for system 10 performance.

(2) The AGCS method eliminates the errors often made by the nurses or physicians while recording the GCS on paper or entering it in a computerized system by hand.

(3) AGCS system 10 may offer very significant savings in personnel costs at the hospital ICUS, ERs, neurology/neuroscience wards, and other sites where the level of consciousness of patients 12 needs to be evaluated at regular intervals.

(4) The AGCS permits more frequent assessment and thus a more rapid response to changes in the patient's status. This in turn could potentially save lives as well as decrease or prevent brain damage.

One might argue that the AGCS device would not significantly improve clinical-decision-making or patient care. This of course might be the case, since the expected output of AGCS system 10 will be nothing more than the old Glasgow Coma Score. By the same argument, however, an automated system for measurement of the non-invasive blood pressure (NBP) of ICU patients 12 will also not contribute to patient care and decision making since such a system yields the same data as a manually taken blood pressure by a nurse. Nevertheless, automated NBP monitoring is done on a regular basis (every 30 min to 1 hour is a standard practice) and is an integral part of all standard physiological monitors in the ICU. Clinical practice has shown that it is very useful in reducing the number of routine measurements performed by the nurses.

There are numerous extensions of AGCS method/system 10 which are expressly included within the scope of the invention. The GCS is commonly used in combination with other neurological tests. For instance, a standard neurological assessment consists of: (1) GCS assessment; (2) motor score; and (3) pupil exam (reactive (+), non-reactive (−), sluggish (sl)). In the future, pure neurophysiological assessments such as EEG activity, and somatosensory and auditory evoked potentials can be incorporated into the coma scoring system. These neurophysiological measurements have been examined in previous studies of trauma patients, and seem to bear some relationship to concurrent neurological condition, and long-term outcome. While EEG (and quantitative EEG), and evoked potential recordings by definition do not play a role in the AGCS paradigm, these electrophysiological measurements should be incorporated in our efforts in the future to quantify severity of neurological injury and the acute degree of neurological impairment. We expect that the optimal automated neurological assessment system 10 will incorporate many of the elements of AGCS as well as continuous quantitative EEG and electrophysiological (EP) assessments. However, for now the GCS is the current clinical standard of care. In addition, the AGCS method can be extended to other scales like RTS (Revised Trauma Scale). The Revised Trauma Score is a physiological scoring system with high inter-observer reliability and demonstrated accuracy in predicting death. It is comprised of the GCS, systolic blood pressure (SBP), and respiratory rate (RR). RTS=0.9368 GCS+0.7326 SBP+0.2908 RR. Using the AGCS method disclosed here an Automatic Revised Trauma Score (ARTS) can be easily computed.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. An apparatus for automated assessment of a degree of consciousness in a patient by automatically determining a Glasgow Coma Score, said apparatus comprising:

a computer having a program stored therein to assess consciousness of said patient; said program comprising an algorithm implementing a decision tree and obtaining a Glasgow Coma Score by coordinating:
  at least one electrode coupled to said computer for sensing a physical response;
  a speaker coupled to said computer for producing an audio signal;
  a microphone coupled to said computer configured to sense an audio response from said patient; and
  a pain stimulator coupled to said computer to generate a pain stimulus in said patient.

2. The apparatus of claim 1 wherein said at least one electrode comprises an EMG electrode.

3. The apparatus of claim 1 wherein said at least one electrode comprises an EOG electrode.

4. The apparatus of claim 2 wherein said at least one electrode comprises an EOG electrode.

5. The apparatus of claim 1 wherein said program stored in said computer provides said computer with speech recognition capability of said audio response from said patient from said microphone.

6. The apparatus of claim 5 wherein said speech recognition capability of said computer comprises a programmed computer with capability to recognize normal conversation.

7. The apparatus of claim 5 wherein said speech recognition capability of said computer comprises a programmed computer with capability to recognize coherent speech.

8. The apparatus of claim 5 wherein said speech recognition capability of said computer comprises a programmed computer with capability to recognize words included in said audio response from said patient.

9. The apparatus of claim 1 wherein said program stored in said computer provides said computer with a capability to record movement of said patient as sensed by said at least one electrode in response to a verbal cue provided by said computer through said speaker.

10. The apparatus of claim 1 wherein said program stored in said computer provides said computer with a capability to record audio responses from said patient as sensed by said microphone in response to a verbal cue provided by said computer through said speaker.

11. The apparatus of claim 1 wherein said program stored in said computer provides said computer with a capability to record movement from said patient as sensed by said at least one electrode and to produce a verbal cue through said speaker in response to said recorded movement.

12. The apparatus of claim 1 wherein said program stored in said computer provides said computer with a capability to produce a verbal cue through said speaker, to record movement or lack thereof from said patient as sensed by said at least one electrode, and in response to said recorded movement or lack thereof to generate said pain stimulus through said pain stimulator.

13. The apparatus of claim 1 wherein said computer performs cycles of stimulation of said patient, recordation of patient response, analysis of patient response and categorization of patient response in which said pain stimulator or speaker is selectively activated to provide a stimulus beginning in a subsequent cycle dependent on categorization of patient response in a prior cycle.

14. A method of automated assessment of a degree of consciousness in a patient using a computer, the method comprising the steps of:

connecting a sensor to the patient and to the computer by a connection;
 automatically determining the Glasgow Coma Score of the patient by computer program control comprising the steps of:

sensing a response from said patient by said sensor;

sending said response through the connection to the computer;

recording said response in said computer, said response being characterizable in nature;

analyzing said characterizable nature of said response to determine said nature in said computer;

categorizing said nature of said response in said computer; and producing by said computer a stimulus dependent on said categorization of said response.

15. The method of claim 14 wherein sensing a response from said patient comprises sensing an audio response by means of a microphone.

16. The method of claim 14 wherein sensing a response from said patient comprises sensing movement by at least one electrode.

17. The method of claim 16 wherein sensing movement by at least one electrode comprises sensing eye movement of said patient.

18. The method of claim 16 wherein sensing movement by at least one electrode comprises muscular movement of said patient.

19. The method of claim 14 wherein producing by said computer a stimulus dependent on said categorization of said response comprises producing an verbal cue.

20. The method of claim 14 wherein producing by said computer a stimulus dependent on said categorization of said response comprises producing pain stimulus.

21. The method of claim 14 wherein categorizing said nature of said response in said computer categorizes said response according to a Glasgow Coma Score.

22. The method of claim 14 wherein said response is an audio response from said patient, wherein said sensor comprises at least a microphone, and wherein analyzing said characterizable nature of said response to determine said nature comprises determining whether said audio response is a normal conversational response to a verbal cue.

23. The method of claim 14 wherein said response is an audio response from said patient, wherein said sensor comprises at least a microphone, and wherein analyzing said characterizable nature of said response to determine said nature comprises determining whether said audio response is a coherent response to a verbal cue.

24. The method of claim 14 wherein said response is an audio response from said patient, wherein said sensor comprises at least a microphone, and wherein analyzing said characterizable nature of said response to determine said nature comprises determining whether said audio response is a recognizable word uttered by said patient in response to a verbal cue.

25. The method of claim 14 wherein said response is a movement by said patient, wherein said sensor comprises at least one body electrode and wherein analyzing said characterizable nature of said response to determine said nature comprises determining whether said movement is an eye opening or not in response to a stimulus.

26. The method of claim 14 wherein said response is a movement by said patient, wherein said sensor comprises at least one body electrode and wherein analyzing said characterizable nature of said response to determine said nature comprises determining whether said movement is a muscular or not in response to a stimulus.

27. The method of claim 26 wherein determining whether said movement is a muscular or not in response to a stimulus comprises determining if there is movement or not to a pain stimulus.

28. The method of claim 26 wherein determining whether said movement is a muscular or not in response to a stimulus comprises determining if there is appropriate movement or not to a verbal stimulus.

29. The method of claim 27 wherein determining if there is appropriate movement or not to a pain stimulus comprises determining by means of at least one body electrode if flexion is normal.

30. The method of claim 27 wherein determining if there is appropriate movement or not to a pain stimulus comprises determining by means of at least one body electrode if flexion is rigid.

31. The method of claim 27 wherein determining if there is appropriate movement or not to a pain stimulus comprises determining by means of at least one body electrode if extension of a limb is normal.

32. An apparatus for automated assessment of a degree of consciousness in a patient by automatically determining a Glasgow Coma Score, said apparatus comprising:

a computer having a program stored therein to assess consciousness of said patient; said program comprising an algorithm implementing a decision tree and obtaining said Glasgow Coma Score by coordinating:

at least one sensor coupled to said computer for sensing a patient response; and at least one stimulator coupled to said computer to generate a stimulus applied to said patient.

* * * * *